(12) United States Patent
Stubbs et al.

(10) Patent No.: US 9,561,378 B2
(45) Date of Patent: Feb. 7, 2017

(54) IMPLANTABLE MEDICAL DEVICE RESPONSIVE TO MRI INDUCED CAPTURE THRESHOLD CHANGES

(71) Applicant: Cardiac Pacemakers, Inc., St. Paul, MN (US)

(72) Inventors: Scott R. Stubbs, Maple Grove, MN (US); Kevin G. Wika, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 170 days.

(21) Appl. No.: 14/053,442

(22) Filed: Oct. 14, 2013

(65) Prior Publication Data

US 2014/0046392 A1  Feb. 13, 2014

Related U.S. Application Data

(62) Division of application No. 12/568,433, filed on Sep. 28, 2009, now Pat. No. 8,571,661.

(60) Provisional application No. 61/102,027, filed on Oct. 2, 2008.

(51) Int. Cl.
*A61N 1/37* (2006.01)
*A61N 1/39* (2006.01)

(52) U.S. Cl.
CPC ............ *A61N 1/3712* (2013.01); *A61N 1/371* (2013.01); *A61N 1/3718* (2013.01); *A61N 1/3943* (2013.01)

(58) Field of Classification Search
CPC .... A61N 1/371; A61N 1/3712; A61N 1/3718; A61N 1/3943
See application file for complete search history.

(56) References Cited

U.S. PATENT DOCUMENTS

| | | |
|---|---|---|
| 3,888,260 A | 6/1975 | Fischell |
| 3,898,995 A | 8/1975 | Dresbach |
| 4,091,818 A | 5/1978 | Brownlee et al. |
| 4,379,459 A | 4/1983 | Stein |
| 4,404,125 A | 9/1983 | Abolins et al. |
| 4,516,579 A | 5/1985 | Irnich |
| 4,611,127 A | 9/1986 | Ibrahim et al. |
| 4,694,837 A | 9/1987 | Blakeley et al. |
| 4,729,376 A | 3/1988 | DeCote, Jr. |
| 4,751,110 A | 6/1988 | Gulla et al. |

(Continued)

FOREIGN PATENT DOCUMENTS

| | | |
|---|---|---|
| EP | 0331959 A2 | 9/1989 |
| EP | 0530006 A1 | 3/1993 |

(Continued)

OTHER PUBLICATIONS

"The Gradient System", downloaded from http://www.medical.siemens.com, 1 page.

(Continued)

*Primary Examiner* — Tammie K Heller
(74) *Attorney, Agent, or Firm* — Schwegman Lundberg & Woessner, P.A.

(57) ABSTRACT

Energy delivered from an implantable medical device to stimulate tissue within a patient's body is controlled. An electrical signal used to stimulate the tissue is changed from a first energy state to a second energy state during a magnetic resonance imaging (MRI) scan. The energy delivered is maintained at the second energy state after the MRI scan. A capture threshold of the tissue is then measured, and the energy delivered to the tissue is adjusted based on the measured capture threshold of the tissue.

20 Claims, 3 Drawing Sheets

(56) References Cited

U.S. PATENT DOCUMENTS

| | | |
|---|---|---|
| 4,779,617 A | 10/1988 | Whigham |
| 4,823,075 A | 4/1989 | Alley |
| 4,841,259 A | 6/1989 | Mayer |
| 4,869,970 A | 9/1989 | Gulla et al. |
| 4,934,366 A | 6/1990 | Truex et al. |
| 5,038,785 A | 8/1991 | Blakeley et al. |
| 5,075,039 A | 12/1991 | Goldberg |
| 5,076,841 A | 12/1991 | Chen et al. |
| 5,120,578 A | 6/1992 | Chen et al. |
| 5,181,511 A | 1/1993 | Nickolls et al. |
| 5,187,136 A | 2/1993 | Klobucar et al. |
| 5,188,117 A | 2/1993 | Steinhaus et al. |
| 5,197,468 A | 3/1993 | Proctor et al. |
| 5,217,010 A | 6/1993 | Tsitlik et al. |
| 5,243,911 A | 9/1993 | Dow et al. |
| 5,279,225 A | 1/1994 | Dow et al. |
| 5,288,313 A | 2/1994 | Portner |
| 5,292,342 A | 3/1994 | Nelson et al. |
| 5,309,096 A | 5/1994 | Hoegnelid |
| 5,325,728 A | 7/1994 | Zimmerman et al. |
| 5,345,362 A | 9/1994 | Winkler |
| 5,391,188 A | 2/1995 | Nelson et al. |
| 5,406,444 A | 4/1995 | Selfried et al. |
| 5,424,642 A | 6/1995 | Ekwall |
| 5,438,900 A | 8/1995 | Sundstrom |
| 5,454,837 A | 10/1995 | Lindegren et al. |
| 5,470,345 A | 11/1995 | Hassler et al. |
| 5,523,578 A | 6/1996 | Herskovic |
| 5,527,348 A | 6/1996 | Winkler et al. |
| 5,529,578 A | 6/1996 | Struble |
| 5,545,187 A | 8/1996 | Bergstrom et al. |
| 5,562,714 A | 10/1996 | Grevious |
| 5,607,458 A | 3/1997 | Causey, III et al. |
| 5,609,622 A | 3/1997 | Soukup et al. |
| 5,618,208 A | 4/1997 | Crouse et al. |
| 5,620,476 A | 4/1997 | Truex et al. |
| 5,647,379 A | 7/1997 | Meltzer |
| 5,649,965 A | 7/1997 | Pons et al. |
| 5,650,759 A | 7/1997 | Hittman et al. |
| 5,662,694 A | 9/1997 | Lidman et al. |
| 5,662,697 A | 9/1997 | Li et al. |
| 5,683,434 A | 11/1997 | Archer |
| 5,687,735 A | 11/1997 | Forbes et al. |
| 5,694,952 A | 12/1997 | Lidman et al. |
| 5,697,958 A | 12/1997 | Paul et al. |
| 5,709,225 A | 1/1998 | Budgifvars et al. |
| 5,714,536 A | 2/1998 | Ziolo et al. |
| 5,722,998 A | 3/1998 | Prutchi et al. |
| 5,727,552 A | 3/1998 | Ryan |
| 5,735,884 A | 4/1998 | Thompson et al. |
| 5,749,910 A | 5/1998 | Brumwell et al. |
| 5,751,539 A | 5/1998 | Stevenson et al. |
| 5,759,197 A | 6/1998 | Sawchuk et al. |
| 5,764,052 A | 6/1998 | Renger |
| 5,766,227 A | 6/1998 | Nappholz et al. |
| 5,776,168 A | 7/1998 | Gunderson |
| 5,782,241 A | 7/1998 | Felblinger et al. |
| 5,782,891 A | 7/1998 | Hassler et al. |
| 5,792,201 A | 8/1998 | Causey, III et al. |
| 5,800,496 A | 9/1998 | Swoyer et al. |
| 5,800,497 A | 9/1998 | Bakels et al. |
| 5,814,090 A | 9/1998 | Latterell et al. |
| 5,817,130 A | 10/1998 | Cox et al. |
| 5,827,997 A | 10/1998 | Chung et al. |
| 5,853,375 A | 12/1998 | Orr |
| 5,867,361 A | 2/1999 | Wolf et al. |
| 5,869,078 A | 2/1999 | Baudino |
| 5,870,272 A | 2/1999 | Seifried et al. |
| 5,871,509 A | 2/1999 | Noren |
| 5,877,630 A | 3/1999 | Kraz |
| 5,895,980 A | 4/1999 | Thompson |
| 5,905,627 A | 5/1999 | Brendel et al. |
| 5,959,829 A | 9/1999 | Stevenson et al. |
| 5,964,705 A | 10/1999 | Truwit et al. |
| 5,968,854 A | 10/1999 | Akopian et al. |
| 5,973,906 A | 10/1999 | Stevenson et al. |
| 5,978,204 A | 11/1999 | Stevenson |
| 5,978,710 A | 11/1999 | Prutchi et al. |
| 5,999,398 A | 12/1999 | Makl et al. |
| 6,008,980 A | 12/1999 | Stevenson et al. |
| 6,031,710 A | 2/2000 | Wolf et al. |
| 6,032,063 A | 2/2000 | Hoar et al. |
| 6,055,455 A | 4/2000 | O'Phelan et al. |
| 6,079,681 A | 6/2000 | Stern et al. |
| 6,101,417 A | 8/2000 | Vogel et al. |
| 6,147,301 A | 11/2000 | Bhatia |
| 6,161,046 A | 12/2000 | Maniglia et al. |
| 6,162,180 A | 12/2000 | Miesel et al. |
| 6,173,203 B1 | 1/2001 | Barkley et al. |
| 6,188,926 B1 | 2/2001 | Vock |
| 6,192,279 B1 | 2/2001 | Barreras, Sr. et al. |
| 6,198,968 B1 | 3/2001 | Prutchi et al. |
| 6,198,972 B1 | 3/2001 | Hartlaub et al. |
| 6,209,764 B1 | 4/2001 | Hartlaub et al. |
| 6,217,800 B1 | 4/2001 | Hayward |
| 6,235,038 B1 | 5/2001 | Hunter et al. |
| 6,245,464 B1 | 6/2001 | Spillman et al. |
| 6,246,902 B1 | 6/2001 | Naylor et al. |
| 6,249,701 B1 | 6/2001 | Rajasekhar et al. |
| 6,268,725 B1 | 7/2001 | Vernon et al. |
| 6,270,831 B2 | 8/2001 | Kumar et al. |
| 6,275,369 B1 | 8/2001 | Stevenson et al. |
| 6,288,344 B1 | 9/2001 | Youker et al. |
| 6,324,431 B1 | 11/2001 | Zarinetchi et al. |
| 6,358,281 B1 | 3/2002 | Berrang et al. |
| 6,365,076 B1 | 4/2002 | Bhatia |
| 6,381,494 B1 | 4/2002 | Gilkerson et al. |
| 6,421,555 B1 | 7/2002 | Nappholz |
| 6,424,234 B1 | 7/2002 | Stevenson |
| 6,446,512 B2 | 9/2002 | Zimmerman et al. |
| 6,452,564 B1 | 9/2002 | Schoen et al. |
| 6,456,481 B1 | 9/2002 | Stevenson |
| 6,459,935 B1 | 10/2002 | Piersma |
| 6,470,212 B1 | 10/2002 | Weijand et al. |
| 6,487,452 B2 | 11/2002 | Legay |
| 6,490,148 B1 | 12/2002 | Allen et al. |
| 6,496,714 B1 | 12/2002 | Weiss et al. |
| 6,503,964 B2 | 1/2003 | Smith et al. |
| 6,506,972 B1 | 1/2003 | Wang |
| 6,510,345 B1 | 1/2003 | Van Bentem |
| 6,512,666 B1 | 1/2003 | Duva |
| 6,522,920 B2 | 2/2003 | Silvian et al. |
| 6,526,321 B1 | 2/2003 | Spehr |
| 6,539,253 B2 | 3/2003 | Thompson et al. |
| 6,545,854 B2 | 4/2003 | Trinh et al. |
| 6,555,745 B1 | 4/2003 | Kruse et al. |
| 6,563,132 B1 | 5/2003 | Talroze et al. |
| 6,566,978 B2 | 5/2003 | Stevenson et al. |
| 6,567,259 B2 | 5/2003 | Stevenson et al. |
| 6,580,947 B1 | 6/2003 | Thompson |
| 6,584,351 B1 | 6/2003 | Ekwall |
| 6,595,756 B2 | 7/2003 | Gray et al. |
| 6,607,485 B2 | 8/2003 | Bardy |
| 6,626,937 B1 | 9/2003 | Cox |
| 6,629,938 B1 | 10/2003 | Engvall et al. |
| 6,631,290 B1 | 10/2003 | Guck et al. |
| 6,631,555 B1 | 10/2003 | Youker et al. |
| 6,640,137 B2 | 10/2003 | MacDonald |
| 6,643,903 B2 | 11/2003 | Stevenson et al. |
| 6,646,198 B2 | 11/2003 | Maciver et al. |
| 6,648,914 B2 | 11/2003 | Berrang et al. |
| 6,662,049 B1 | 12/2003 | Miller |
| 6,673,999 B1 | 1/2004 | Wang et al. |
| 6,711,440 B2 | 3/2004 | Deal et al. |
| 6,713,671 B1 | 3/2004 | Wang et al. |
| 6,718,203 B2 | 4/2004 | Weiner et al. |
| 6,718,207 B2 | 4/2004 | Connelly |
| 6,725,092 B2 | 4/2004 | MacDonald et al. |
| 6,731,979 B2 | 5/2004 | MacDonald |
| 6,795,730 B2 | 9/2004 | Connelly et al. |
| 6,901,292 B2 | 5/2005 | Hrdlicka et al. |
| 6,925,328 B2 | 8/2005 | Foster et al. |
| 6,937,906 B2 | 8/2005 | Terry et al. |
| 6,944,489 B2 | 9/2005 | Zeijlemaker et al. |

(56) References Cited

U.S. PATENT DOCUMENTS

| | | |
|---|---|---|
| 6,963,779 B1 | 11/2005 | Shankar |
| 7,013,180 B2 | 3/2006 | Dublin et al. |
| 7,020,517 B2 | 3/2006 | Weiner |
| 7,050,855 B2 | 5/2006 | Zeijlemaker et al. |
| 7,076,283 B2 | 7/2006 | Cho et al. |
| 7,082,328 B2 | 7/2006 | Funke |
| 7,092,756 B2 | 8/2006 | Zhang et al. |
| 7,123,013 B2 | 10/2006 | Gray |
| 7,138,582 B2 | 11/2006 | Lessar et al. |
| 7,164,950 B2 | 1/2007 | Kroll et al. |
| 7,174,219 B2 | 2/2007 | Wahlstrand et al. |
| 7,174,220 B1 | 2/2007 | Chitre et al. |
| 7,212,863 B2 | 5/2007 | Strandberg |
| 7,231,251 B2 | 6/2007 | Yonce et al. |
| 7,242,981 B2 | 7/2007 | Ginggen |
| 7,272,444 B2 | 9/2007 | Peterson et al. |
| 7,369,898 B1 | 5/2008 | Kroll et al. |
| 7,388,378 B2 | 6/2008 | Gray et al. |
| 7,509,167 B2 | 3/2009 | Stessman |
| 7,561,915 B1 | 7/2009 | Cooke et al. |
| 7,801,625 B2 | 9/2010 | MacDonald |
| 7,835,803 B1 | 11/2010 | Malinowski et al. |
| 7,839,146 B2 | 11/2010 | Gray |
| 8,014,867 B2 | 9/2011 | Cooke et al. |
| 8,032,228 B2 | 10/2011 | Ameri et al. |
| 8,086,321 B2 | 12/2011 | Ameri |
| 8,121,705 B2 | 2/2012 | MacDonald |
| 8,160,717 B2 | 4/2012 | Ameri |
| 8,311,637 B2 | 11/2012 | Ameri |
| 8,543,207 B2 | 9/2013 | Cooke et al. |
| 8,554,335 B2 | 10/2013 | Ameri et al. |
| 8,565,874 B2 | 10/2013 | Stubbs et al. |
| 8,571,661 B2 | 10/2013 | Stubbs et al. |
| 8,639,331 B2 | 1/2014 | Stubbs et al. |
| 2001/0002000 A1 | 5/2001 | Kumar et al. |
| 2001/0006263 A1 | 7/2001 | Hayward |
| 2001/0011175 A1 | 8/2001 | Hunter et al. |
| 2001/0018123 A1 | 8/2001 | Furumori et al. |
| 2001/0025139 A1 | 9/2001 | Pearlman |
| 2001/0037134 A1 | 11/2001 | Munshi |
| 2001/0050837 A1 | 12/2001 | Stevenson et al. |
| 2002/0019658 A1 | 2/2002 | Munshi |
| 2002/0026224 A1 | 2/2002 | Thompson et al. |
| 2002/0038135 A1 | 3/2002 | Connelly et al. |
| 2002/0050401 A1 | 5/2002 | Youker et al. |
| 2002/0072769 A1 | 6/2002 | Silvian et al. |
| 2002/0082648 A1 | 6/2002 | Kramer et al. |
| 2002/0102835 A1 | 8/2002 | Stucchi et al. |
| 2002/0116028 A1 | 8/2002 | Greatbatch et al. |
| 2002/0116029 A1 | 8/2002 | Miller et al. |
| 2002/0116033 A1 | 8/2002 | Greatbatch et al. |
| 2002/0116034 A1 | 8/2002 | Miller et al. |
| 2002/0117314 A1 | 8/2002 | Maciver et al. |
| 2002/0128689 A1 | 9/2002 | Connelly et al. |
| 2002/0128691 A1 | 9/2002 | Connelly |
| 2002/0133086 A1 | 9/2002 | Connelly et al. |
| 2002/0133199 A1 | 9/2002 | MacDonald et al. |
| 2002/0133200 A1 | 9/2002 | Weiner et al. |
| 2002/0133201 A1 | 9/2002 | Connelly et al. |
| 2002/0133202 A1 | 9/2002 | Connelly et al. |
| 2002/0133208 A1 | 9/2002 | Connelly |
| 2002/0133211 A1 | 9/2002 | Weiner et al. |
| 2002/0133216 A1 | 9/2002 | Connelly et al. |
| 2002/0138102 A1 | 9/2002 | Weiner et al. |
| 2002/0138107 A1 | 9/2002 | Weiner et al. |
| 2002/0138108 A1 | 9/2002 | Weiner et al. |
| 2002/0138110 A1 | 9/2002 | Connelly et al. |
| 2002/0138112 A1 | 9/2002 | Connelly et al. |
| 2002/0138113 A1 | 9/2002 | Connelly et al. |
| 2002/0138124 A1 | 9/2002 | Helfer et al. |
| 2002/0143258 A1 | 10/2002 | Weiner et al. |
| 2002/0147388 A1 | 10/2002 | Mass et al. |
| 2002/0147470 A1 | 10/2002 | Weiner et al. |
| 2002/0162605 A1 | 11/2002 | Horton et al. |
| 2002/0166618 A1 | 11/2002 | Wolf et al. |
| 2002/0175782 A1 | 11/2002 | Trinh et al. |
| 2002/0183796 A1 | 12/2002 | Connelly |
| 2002/0198569 A1 | 12/2002 | Foster et al. |
| 2003/0036774 A1 | 2/2003 | Maier et al. |
| 2003/0036776 A1 | 2/2003 | Foster et al. |
| 2003/0045907 A1 | 3/2003 | MacDonald |
| 2003/0053284 A1 | 3/2003 | Stevenson et al. |
| 2003/0055457 A1 | 3/2003 | MacDonald |
| 2003/0056820 A1 | 3/2003 | MacDonald |
| 2003/0074029 A1 | 4/2003 | Deno et al. |
| 2003/0081370 A1 | 5/2003 | Haskell et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0083728 A1 | 5/2003 | Greatbatch et al. |
| 2003/0100925 A1 | 5/2003 | Pape et al. |
| 2003/0109901 A1 | 6/2003 | Greatbatch |
| 2003/0111142 A1 | 6/2003 | Horton et al. |
| 2003/0114897 A1 | 6/2003 | Von Arx et al. |
| 2003/0114898 A1 | 6/2003 | Von Arx et al. |
| 2003/0120197 A1 | 6/2003 | Kaneko et al. |
| 2003/0130647 A1 | 7/2003 | Gray et al. |
| 2003/0130700 A1 | 7/2003 | Miller et al. |
| 2003/0130701 A1 | 7/2003 | Miller |
| 2003/0130708 A1 | 7/2003 | Von Arx et al. |
| 2003/0135114 A1 | 7/2003 | Pacetti et al. |
| 2003/0135160 A1 | 7/2003 | Gray et al. |
| 2003/0139096 A1 | 7/2003 | Stevenson et al. |
| 2003/0140931 A1 | 7/2003 | Zeijlemaker et al. |
| 2003/0144704 A1 | 7/2003 | Terry et al. |
| 2003/0144705 A1 | 7/2003 | Funke |
| 2003/0144706 A1 | 7/2003 | Funke |
| 2003/0144716 A1 | 7/2003 | Reinke et al. |
| 2003/0144717 A1 | 7/2003 | Hagele |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0149459 A1 | 8/2003 | Von Arx et al. |
| 2003/0158584 A1 | 8/2003 | Cates et al. |
| 2003/0176900 A1 | 9/2003 | MacDonald |
| 2003/0179536 A1 | 9/2003 | Stevenson et al. |
| 2003/0191505 A1 | 10/2003 | Gryzwa et al. |
| 2003/0195570 A1 | 10/2003 | Deal et al. |
| 2003/0199755 A1 | 10/2003 | Halperin et al. |
| 2003/0204207 A1 | 10/2003 | MacDonald et al. |
| 2003/0204215 A1 | 10/2003 | Gunderson et al. |
| 2003/0204217 A1 | 10/2003 | Greatbatch |
| 2003/0213604 A1 | 11/2003 | Stevenson et al. |
| 2003/0213605 A1 | 11/2003 | Brendel et al. |
| 2004/0005483 A1 | 1/2004 | Lin |
| 2004/0015162 A1 | 1/2004 | McGaffigan |
| 2004/0015197 A1 | 1/2004 | Gunderson |
| 2004/0019273 A1 | 1/2004 | Helfer et al. |
| 2004/0049237 A1 | 3/2004 | Larson et al. |
| 2004/0088012 A1 | 5/2004 | Kroll et al. |
| 2004/0093432 A1 | 5/2004 | Luo et al. |
| 2004/0263174 A1 | 12/2004 | Gray et al. |
| 2005/0043761 A1 | 2/2005 | Connelly et al. |
| 2005/0070787 A1 | 3/2005 | Zeijlemaker |
| 2005/0070975 A1 | 3/2005 | Zeijlemaker et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0197677 A1 | 9/2005 | Stevenson |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2006/0025820 A1 | 2/2006 | Phillips et al. |
| 2006/0030774 A1 | 2/2006 | Gray et al. |
| 2006/0041294 A1 | 2/2006 | Gray |
| 2006/0167496 A1 | 7/2006 | Nelson et al. |
| 2006/0173295 A1 | 8/2006 | Zeijlemaker |
| 2006/0247747 A1 | 11/2006 | Olsen et al. |
| 2006/0247748 A1 | 11/2006 | Wahlstrand et al. |
| 2006/0271138 A1 | 11/2006 | MacDonald |
| 2006/0293591 A1 | 12/2006 | Wahlstrand et al. |
| 2007/0019354 A1 | 1/2007 | Kamath |

(56) References Cited

U.S. PATENT DOCUMENTS

| | | |
|---|---|---|
| 2007/0021814 A1 | 1/2007 | Inman et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0203523 A1 | 8/2007 | Betzold |
| 2007/0238975 A1 | 10/2007 | Zeijlemaker |
| 2007/0255332 A1 | 11/2007 | Cabelka et al. |
| 2008/0033497 A1 | 2/2008 | Bulkes et al. |
| 2008/0132985 A1 | 6/2008 | Wedan et al. |
| 2008/0154342 A1 | 6/2008 | Digby et al. |
| 2008/0221638 A1 | 9/2008 | Wedan et al. |
| 2008/0234772 A1 | 9/2008 | Shuros et al. |
| 2009/0138058 A1 | 5/2009 | Cooke et al. |
| 2009/0149906 A1 | 6/2009 | Ameri et al. |
| 2009/0149909 A1 | 6/2009 | Ameri |
| 2009/0157146 A1 | 6/2009 | Linder et al. |
| 2009/0204182 A1 | 8/2009 | Ameri |
| 2009/0210025 A1 | 8/2009 | Ameri |
| 2010/0087892 A1 | 4/2010 | Stubbs et al. |
| 2010/0211123 A1 | 8/2010 | Stubbs et al. |
| 2011/0137359 A1 | 6/2011 | Stubbs et al. |
| 2011/0270338 A1 | 11/2011 | Cooke et al. |
| 2011/0276104 A1 | 11/2011 | Ameri et al. |
| 2012/0071941 A1 | 3/2012 | Ameri |
| 2012/0253425 A1 | 10/2012 | Yoon et al. |
| 2014/0018870 A1 | 1/2014 | Cooke et al. |
| 2014/0046390 A1 | 2/2014 | Stubbs et al. |
| 2014/0135861 A1 | 5/2014 | Stubbs et al. |

FOREIGN PATENT DOCUMENTS

| | | |
|---|---|---|
| EP | 0591334 A1 | 4/1994 |
| EP | 0331959 B1 | 12/1994 |
| EP | 0705621 A1 | 4/1996 |
| EP | 0891786 A2 | 1/1999 |
| EP | 0891207 B1 | 11/1999 |
| EP | 0980105 A1 | 2/2000 |
| EP | 0989623 A1 | 3/2000 |
| EP | 0989624 A1 | 3/2000 |
| EP | 1007132 A2 | 6/2000 |
| EP | 1109180 A2 | 6/2001 |
| EP | 1128764 A1 | 9/2001 |
| EP | 0705621 B1 | 1/2002 |
| EP | 1191556 A2 | 3/2002 |
| EP | 1271579 A2 | 1/2003 |
| EP | 0719570 B1 | 4/2003 |
| EP | 1308971 A2 | 5/2003 |
| EP | 1007140 B1 | 10/2003 |
| EP | 1372782 A2 | 1/2004 |
| EP | 0870517 B1 | 6/2004 |
| EP | 1061849 B1 | 11/2005 |
| EP | 1060762 B1 | 8/2006 |
| EP | 0836413 B1 | 8/2008 |
| WO | WO9104069 A1 | 4/1991 |
| WO | WO9638200 A1 | 12/1996 |
| WO | WO9712645 A1 | 4/1997 |
| WO | WO0054953 A1 | 9/2000 |
| WO | WO0137286 A1 | 5/2001 |
| WO | WO0180940 A1 | 11/2001 |
| WO | WO0186774 A1 | 11/2001 |
| WO | WO02056761 A2 | 7/2002 |
| WO | WO02065895 A2 | 8/2002 |
| WO | WO02072004 A2 | 9/2002 |
| WO | WO02089665 A1 | 11/2002 |
| WO | WO02092161 A1 | 11/2002 |
| WO | WO03013199 A2 | 2/2003 |
| WO | WO03037399 A2 | 5/2003 |
| WO | WO03059445 A2 | 7/2003 |
| WO | WO03061755 A2 | 7/2003 |
| WO | WO03063258 A1 | 7/2003 |
| WO | WO-03063946 A2 | 8/2003 |
| WO | WO03063946 A2 | 8/2003 |
| WO | WO03063952 A2 | 8/2003 |
| WO | WO03063954 A1 | 8/2003 |
| WO | WO03063955 A1 | 8/2003 |
| WO | WO03063956 A2 | 8/2003 |
| WO | WO03063958 A1 | 8/2003 |
| WO | WO03063962 A1 | 8/2003 |
| WO | WO-03070098 A1 | 8/2003 |
| WO | WO03070098 A2 | 8/2003 |
| WO | WO03073449 A1 | 9/2003 |
| WO | WO03073450 A1 | 9/2003 |
| WO | WO03086538 A1 | 10/2003 |
| WO | WO03090846 A2 | 11/2003 |
| WO | WO03090854 A1 | 11/2003 |
| WO | WO03095022 A2 | 11/2003 |
| WO | WO2006124481 A2 | 11/2006 |

OTHER PUBLICATIONS

Dempsey Mary F. et al., "Investigation of the Factors Responsible for Burns During MRI", Journal of Magnetic Resonance Imaging 2001;13:627-631.

File History for U.S. Appl. No. 11/015,807, filed Dec. 17, 2004.

Hebrank FX, Gebhardt M. Safe model: a new method for predicting peripheral nerve stimulations in MRI (abstr) in: Proceedings of the Eighth Meeting of the International Society for Magnetic Resonance in Medicine. Berkeley, Calif: International Society for Magnetic Resonance in Medicine, 2000; 2007.

International Search Report and Written Opinion issued in PCT/US2009/059093, mailed Dec. 29, 2009.

International Search Report and Written Opinion issued in PCT/US2009/068314, mailed Mar. 25, 2009, 14 pages.

International Search Report and Written Opinion issued in PCT/US2010/053202, mailed Dec. 30, 2010, 12 pages.

Kerr, Martha, "Shock Rate Cut 70% With ICDs Programmed to First Deliver Antitachycardia Pacing: Results of the PainFREE Rx II Trial," Medscape CRM News, May 21, 2003.

Luechinger, Roger et al., "In vivo heating of pacemaker leads during magnetic resonance imaging", European Heart Journal 2005;26:376-383.

Nyenhuis, John A. et al., "MRI and Implantable Medical Devices: Basic Interactions With an Emphasis on Heting", IEEE Transactions on Device and Materials Reliability, vol. 5, No. Sep. 2005, pp. 467-480.

Schueler, et al., "MRI Compatibility and Visibility Assessment of Implantable Medical Devices", Journal of Magnetic Resonance Imaging, 9:596-603 (1999).

Shellock FG, "Reference manual for magnetic resonance safety, implants, and devices", pp. 136-139, 2008 ed. Los Angeles; Biomedical Research Publishing Group; 2008.

Shellock, Frank G. et al., "Cardiovascular catheters and accessories: ex vivo testing of ferromagnetism, heating, and artifacts associated with MRI", Journal of Magnetic Resonance Imaging, Nov./Dec. 1998; 8:1338-1342.

Sweeney, Michael O. et al., Appropriate and Inappropriate Ventricular Therapies, Quality of Life, and Mortality Among Primary and Secondary Prevention Implantable Cardioverter Defibrillator Patients: Results From the Pacing Fast VT Reduces Shock Therapies (PainFREE Rx II) Trial, American Heart Association, 2005.

Wilkoff, Bruce L. et al., "A Comparison of Empiric to Physician-Tailored Programming of Implantable Cardioverter-Defibrillators Results From the Prospective Randomized Multicenter Empiric Trial," Journal of the American College of Cardiology vol. 48, No. 2, 2006. doi:10.1016/j.jacc.2006.03.037.

"U.S. Appl. No. 12/568,433, Advisory Action mailed Nov. 16, 2012", 3 pgs.

"U.S. Appl. No. 12/568,433, Appeal Brief filed Apr. 12, 2013", 22 pgs.

"U.S. Appl. No. 12/568,433, Appeal Decision mailed Mar. 12, 2013", 2 pgs.

"U.S. Appl. No. 12/568,433, Final Office Action mailed Sep. 24, 2012", 8 pgs.

"U.S. Appl. No. 12/568,433, Non Final Office Action mailed May 7, 2012", 8 pgs.

"U.S. Appl. No. 12/568,433, Notice of Allowance mailed Jun. 28, 2013", 6 pgs.

(56) References Cited

OTHER PUBLICATIONS

"U.S. Appl. No. 12/568,433, Pre-Appeal Brief Request filed Dec. 20, 2012", 4 pgs.
"U.S. Appl. No. 12/568,433, Preliminary Amendment filed Apr. 1, 2011", 5 pgs.
"U.S. Appl. No. 12/568,433, Response filed Mar. 26, 2012 to Restriction Requirement mailed Mar. 16, 2012", 1 pg.
"U.S. Appl. No. 12/568,433, Response filed Jul. 19, 2012 to Non Final Office Action mailed May 7, 2012", 7 pgs.
"U.S. Appl. No. 12/568,433, Response filed Nov. 8, 2012 to Final Office Action mailed Sep. 24, 2012", 7 pgs.
"U.S. Appl. No. 12/568,433, Restriction Requirement mailed Mar. 16, 2012", 6 pgs.
"European Application Serial No. 09793203.2, Examination Notification Art. 94(3) mailed May 25, 2012", 4 pgs.
"European Application Serial No. 09793203.2, Noting of loss of rights mailed Apr. 29, 2015", 1 pg.
"European Application Serial No. 09793203.2, Office Action mailed Jul. 13, 2011", 2 pgs.
"European Application Serial No. 09793203.2, Response filed Jan. 13, 2012 to Office Action mailed Jul. 13, 2011", 12 pgs.
"European Application Serial No. 09793203.2, Response filed Nov. 28, 2012 to Examination Notification Art. 94(3) mailed May 25, 2012", 12 pgs.
"International Application Serial No. PCT/US2009/059093, International Preliminary Report on Patentability mailed Apr. 14, 2011", 8 pgs.

IMPLANTABLE MEDICAL DEVICE RESPONSIVE TO MRI INDUCED CAPTURE THRESHOLD CHANGES

CROSS-REFERENCE TO RELATED APPLICATION

This application is a division of U.S. application Ser. No. 12/568,433, filed Sep. 28, 2009, now issued as U.S. Pat. No. 8,571,661, which claims priority to U.S. Provisional Application 61/102,027, filed Oct. 2, 2008, which are herein incorporated by reference in their entirety.

TECHNICAL FIELD

The present invention relates to implantable medical devices. More particularly, the present invention relates to implantable medical devices that detect and compensate for magnetic resonance imaging (MRI) induced capture threshold changes.

BACKGROUND

Magnetic resonance imaging (MRI) is a non-invasive imaging method that utilizes nuclear magnetic resonance techniques to render images within a patient's body. Typically, MRI systems employ the use of a magnetic coil having a magnetic field strength of between about 0.2 to 3.0 Tesla. During the procedure, the body tissue is also briefly exposed to radio frequency (RF) pulses of electromagnetic energy. The relaxation of proton spins following cessation of the RF pulses can be used to image the body tissue.

During imaging, the electromagnetic radiation produced by the MRI system can be picked up by implantable device leads used in implantable medical devices such as pacemakers or cardiac defibrillators. This energy may be transferred through the lead to the electrode in contact with the tissue, which can cause elevated temperatures at the point of contact. The degree of tissue heating is typically related to factors such as the length of the lead, the conductivity or impedance of the lead, and the surface area of the lead electrodes. The effectiveness of implanted cardiac management devices may be compromised by the heating of cardiac tissue at the lead/heart interface. For example, pacemakers deliver low energy pace pulses that cause the heart to initiate a beat. The minimum voltage of those pace pulses that results in a response from the heart is known as the capture threshold. The capture threshold may increase as a result of localized heating of the lead due to the MRI RF field. Consequently, with an elevated capture threshold for the cardiac tissue, the implantable medical device may not deliver a pulse of sufficient voltage to generate a desired response in the tissue (i.e., loss of capture).

SUMMARY

In one aspect, the present invention relates to controlling energy delivered from an implantable medical device to stimulate tissue within a patient's body. An electrical signal used to stimulate the tissue is changed from a first energy state to a second energy state during a magnetic resonance imaging (MRI) scan. The energy delivered is maintained at the second energy state after the MRI scan. A capture threshold of the tissue is then measured, and the energy delivered to the tissue is adjusted based on the measured capture threshold of the tissue.

In another aspect, the present invention relates to controlling energy delivered from an implantable medical device to stimulate tissue. Energy having a first energy state is delivered to stimulate the tissue. Magnetic resonance imaging (MRI) scan fields (e.g., magnetic and/or electromagnetic fields) are detected, and the energy delivered is increased from the first energy state to a second energy state. The energy delivered is maintained at the second energy state after the MRI scan fields are no longer detected. A capture threshold of the tissue is then measured, and the energy delivered by the implantable medical device is adjusted, if necessary, based on the measured capture threshold of the tissue.

In a further aspect, the present invention relates to an implantable medical device including an electrode configured to contact tissue in a body vessel and a lead having a lead conductor connected to the electrode. Sensing circuitry receives signals through the lead based on electrical activity of the tissue, and therapy circuitry delivers electrical stimulation to the tissue through the lead. Magnetic field detection circuitry detects magnetic resonance imaging (MRI) scan fields. Control circuitry is operable to set a level of energy delivered by the therapy circuitry to stimulate the tissue to an MRI mode energy state when the magnetic detection circuitry detects the MRI scan fields. After the magnetic field detection circuitry no longer detects the MRI scan fields, the control circuitry adjusts the level of energy delivered based on a capture threshold of the tissue periodically measured by the sensing circuitry.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
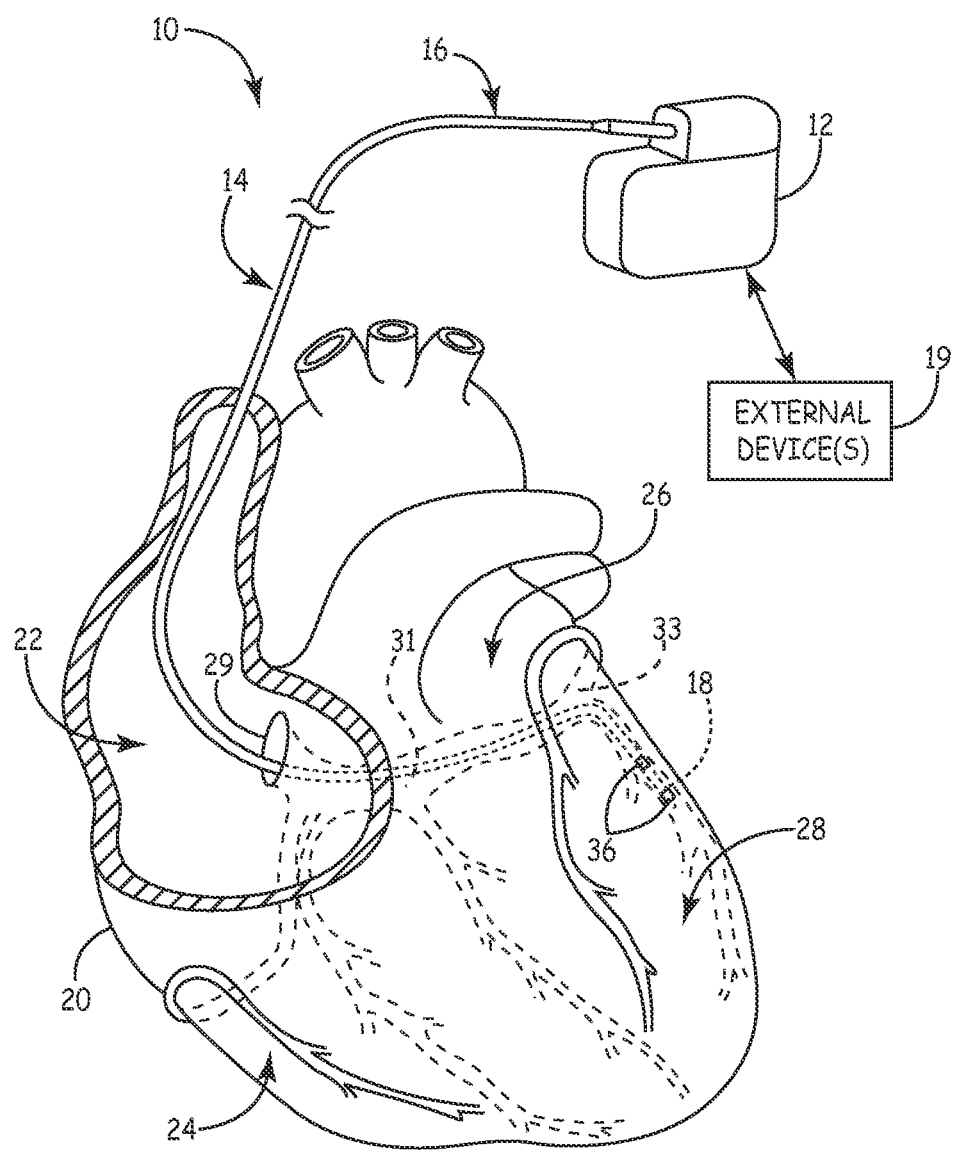
FIG. 1 is a schematic drawing of a cardiac rhythm management system including a pulse generator coupled to a lead deployed in a patient's heart.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a cardiac rhythm management system 10 including an implantable medical device (IMD) 12 with a lead 14 having a proximal end 16 and a distal end 18. In one embodiment, the IMD 12 includes a pulse generator. The IMD 12 can be implanted subcutaneously within the body, typically at a location such as in the patient's chest or abdomen, although other implantation locations are possible. The proximal end 16 of the lead 14 can be coupled to or formed integrally with the IMD 12. The distal end 18 of the lead 14, in turn, can be implanted at a desired location in or near the heart 16. The system 10 may also include one or more external devices 19 (e.g., a computing device and/or programming device), which may communicate with the IMD 12 from outside of the patient's body wirelessly.

As shown in FIG. 1, distal portions of lead 14 are disposed in a patient's heart 20, which includes a right atrium 22, a right ventricle 24, a left atrium 26, and a left ventricle 28. In the embodiment illustrated in FIG. 1, the distal end 18 of the lead 14 is transvenously guided through the right atrium 22, through the coronary sinus ostium 29, and into a branch of the coronary sinus 31 or the great cardiac vein 33. The illustrated position of the lead 14 can be used for sensing or for delivering pacing and/or defibrillation energy to the left side of the heart 20, or to treat arrhythmias or other cardiac disorders requiring therapy delivered to the left side of the heart 20. Additionally, while the lead 14 is shown disposed in the left ventricle 28 of the heart, the lead 14 can alternatively be used to provide treatment in other regions of the heart 20 (e.g., the right ventricle 24).

Although the illustrative embodiment depicts only a single lead 14 inserted into the patient's heart 20, it should be understood that multiple leads can be utilized so as to electrically stimulate other areas of the heart 20. In some embodiments, for example, the distal end of a second lead (not shown) may be implanted in the right atrium 18. In addition, or in lieu, another lead may be implanted in or near the right side of the heart 20 (e.g., in the coronary veins) to stimulate the right side of the heart 20. Other types of leads such as epicardial leads may also be utilized in addition to, or in lieu of, the lead 14 depicted in FIG. 1.

During operation, the lead 14 can be configured to convey electrical signals between the IMD 12 and the heart 20. For example, in those embodiments where the IMD 12 is a pacemaker, the lead 14 can be utilized to deliver electrical therapeutic stimulus for pacing the heart 20. In those embodiments where the IMD 12 is an implantable cardiac defibrillator, the lead 14 can be utilized to deliver electric shocks to the heart 20 in response to an event such as a heart attack or arrhythmia. In some embodiments, the IMD 12 includes both pacing and defibrillation capabilities.

When the IMD 12 is subjected to a magnetic field from an MRI scanner or other external magnetic source, electromagnetic radiation is delivered to the patient's body that can be picked up by the lead 14 and transferred to one or more lead electrodes 36 in contact with the body tissue. This electromagnetic radiation can cause heating at the interface of the lead electrodes 36 and body tissue. This can affect the capture threshold of the heart 20, which is the stimulus amplitude and/or duration of the electrical signals provided by the IMD 12 to the heart 20 that cause the heart 20 to beat.

Figure 2:
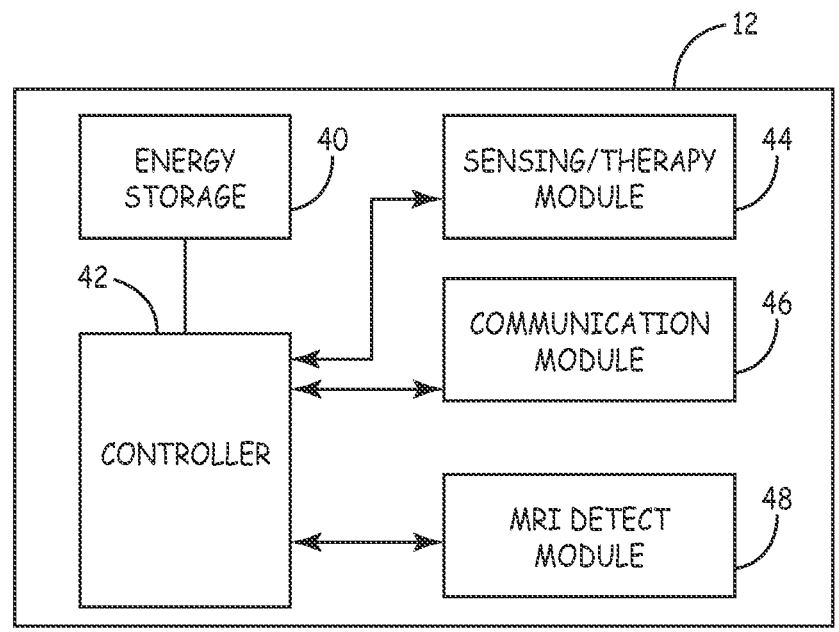
FIG. 2 is a functional block diagram of an implantable medical device configured to detect and compensate for magnetic resonance imaging (MRI) induced capture threshold changes according to an embodiment of the present invention.

FIG. 2 is a functional block diagram of an embodiment of the IMD 12 configured to detect and compensate for MRI induced capture threshold changes. The IMD 12 includes an energy storage device 40, a controller 42, a sensing/therapy module 44, a communication module 46, and an MRI detect module 48. The term "module" is not intended to imply any particular structure. Rather, "module" may mean components and circuitry integrated into a single unit as well as individual, discrete components and circuitry that are functionally related. In addition, it should be noted that IMD 12 may include additional functional modules that are operable to perform other functions associated with operation of IMD 12.

The energy storage device 40 operates to provide operating power to the controller 42, the sensing/therapy module 44, the communication module 46, and the MRI detect module 48. The controller 42 operates to control the sensing/therapy module 44, the communication module 46, and the MRI detect module 48, each of which is operatively coupled to and communicates with the controller 42. For example, the controller 42 may command the sensing/therapy module 44 to deliver a desired therapy, such as a pacing or defibrillation stimulus, or to determine the capture threshold of the tissue to which the electrodes 36 are coupled. In addition, the controller 42 may command the communication module 46 to transmit and/or receive data from the external device 19. Furthermore, the controller 42 may receive signals from the MRI detect module 48 indicating the presence or absence of electromagnetic radiation generated by an MRI scan.

The IMD 12 may also include timing circuitry (not shown) which operates to schedule, prompt, and/or activate the IMD 12 to perform various activities. In one embodiment, the timing circuitry is an internal timer or oscillator, while in other embodiments, timing may be performed by specific hardware components that contain hardwired logic for performing the steps, or by any combination of programmed computer components and custom hardware components.

The communication module 46 is configured to both transmit and receive telemetry signals to and from other devices, such as the external device 19. In other embodiments, the IMD 12 includes at least one transducer configured for receiving a telemetry signal and at least one transducer for transmitting a telemetry signal. The wireless transducer 26 may be any type of device capable of sending and/or receiving information via a telemetry signal, including, but not limited to, a radio frequency (RF) transmitter, an acoustic transducer, or an inductive transducer.

The sensing/therapy module 44 operates to perform the therapeutic and/or diagnostic functions of the IMD 12. In one embodiment, the sensing/therapy module 44 delivers a cardiac pacing and/or defibrillation stimulus. The sensing/therapy module 44 is not limited to performing any particular type of physiologic measurement or therapy, and may be configured to perform other types of physiologic measurements and therapy, such as neurological measurements and therapy. The sensing/therapy module 44 is also operable to automatically determine the capture threshold of the heart 20 by providing a pacing stimulus to the heart 20 and sensing whether the stimulus results in a contraction of the heart 20. In some embodiments, the sensing/therapy module 44 delivers a sequence of pacing pulses of varying magnitude and/or duration to the heart 20 and senses a response of the tissue to the pacing pulses to determine whether the pulses have a large enough duration and/or magnitude to stimulate the heart 20. One example circuit arrangement that may be included in sensing/therapy module 44 to determine the capture threshold of heart 20 is disclosed in U.S. Pat. No. 7,092,756, entitled "Autocapture Pacing/Sensing Configuration," which is incorporated herein by reference in its entirety.

The MRI detect module 48 senses the presence of the magnetic and/or electromagnetic fields associated with an MRI scan. In some embodiments, the MRI detect module 48 includes a power inductor and a core saturation detector.

When the power inductor saturates in the presence of an MRI field, the inductance of the power inductor decreases, which is detected by the core saturation detector. One example module having such a configuration that is suitable for use in MRI detect module 48 is disclosed in U.S. patent application Ser. No. 11/276,159, entitled "MRI Detector for Implantable Medical Device," which is incorporated herein by reference in its entirety. Any type of sensor or device may alternatively or additionally be incorporated into the MRI detect module 48 that is operable to detect the presence of MRI fields. Example sensors or devices that may be included in the MRI detect module 48 include, but are not limited to, a Hall effect sensor, a magnetotransistor, a magnetodiode, a magneto-optical sensor, and/or a giant magnetoresistive sensor.

When the MRI detect module 48 detects the presence of an MRI field, the MRI detect module 48 sends a signal to the controller 42. The controller 42 may then switch operation of the IMD 12 from a normal mode of operation to an MRI mode of operation. Alternatively, the IMD 12 may be programmed to the MRI mode of operation, for example by using the external device 19. The MRI mode of operation may include non-sensing fixed rate bradycardia pacing (described in more detail below), disablement of tachycardia therapy, or any mode of operation that is safe and desirable in a high electromagnetic field environment where sensing of cardiac activity may be compromised.

Figure 3:
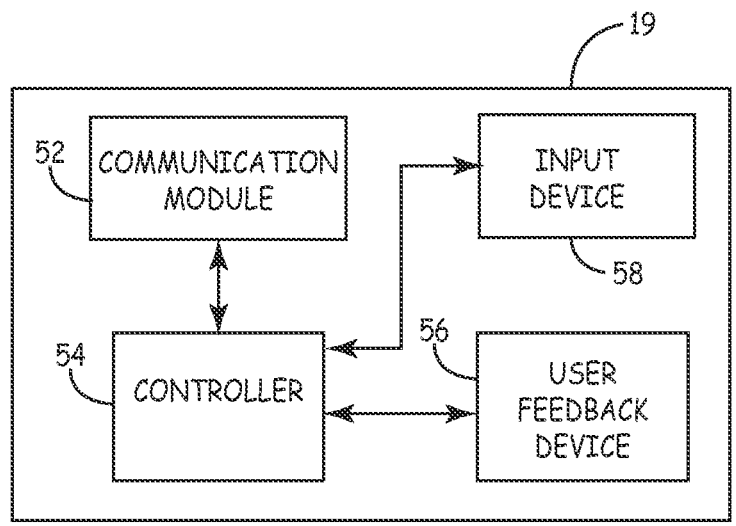
FIG. 3 is a functional block diagram of an external device operable to communicate with the implantable medical device of FIG. 2.

FIG. 3 is a functional block diagram illustrating an embodiment of the external device 19 shown in FIG. 1. The external device 19 includes a communication module 52, a controller 54, an audio/visual user feedback device 56, and an input device 58. In some embodiments, the external device 19 is a device for use by a caregiver for communicating with the IMD 12. The external device 19 may include an interface for connecting to the Internet, to a cell phone, and/or to other wired or wireless means for downloading or uploading information and programs, debugging data, and upgrades.

The communication module 52 for the external device 19 is configured to both transmit and receive signals to and from the IMD 12. In other embodiments, the external device 19 includes at least one transducer configured to receive a signal and at least one transducer for transmitting a signal. The communication module 52 may be any type of device capable of communicating with the communication module 46 of the IMD 12 including, but not limited to, an RF transmitter, an acoustic transducer, or an inductive transducer.

In some embodiments, the controller 54 includes a processor for analyzing, interpreting, and/or processing the received signals, and a memory for storing the processed information and/or commands for use internally. For example, the controller 54 may be used to analyze signals related to the capture threshold of the heart 20 from the IMD 12. The controller 54 can be configured as a digital signal processor (DSP), a field programmable gate array (FPGA), an application specific integrated circuit (ASIC) compatible device such as a CoolRISC processor available from Xemics or other programmable devices, and/or any other hardware components or software modules for processing, analyzing, storing data, and controlling the operation of the external device 19.

The user feedback device 56 may include a screen or display panel for communicating information to the clinician and/or to the patient. In some embodiments, the screen or display panel is configured to display operational information about the IMD 12. For example, the screen or display panel may display visual information indicative of the capture threshold of the heart 20 as received from the IMD 12 for use in assessing whether the active pacing signals are sufficient to stimulate the heart 20.

The input device 58 includes an interface through which a clinician may input information or commands to be executed by the external device 19. In some embodiments, the input device 58 is a keyboard. For example, if information about the capture threshold test conducted by the sensing/therapy module 44 of the IMD 12 is provided on the user feedback device 56, the clinician may provide an input to the external device 19 through the input device 58 to communicate pacing signal configuration information to the IMD 12 based on the information about the capture threshold test.

Figure 4:
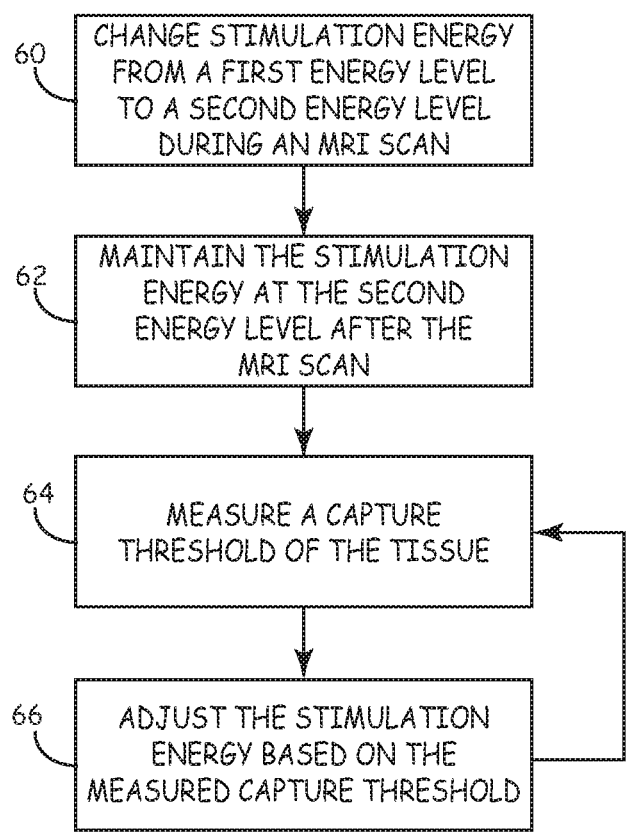
FIG. 4 is a flow diagram of a process for compensating for magnetic resonance imaging (MRI) induced capture threshold changes according to an embodiment of the present invention.

FIG. 4 is a flow diagram of a process for controlling the IMD 12 during and after an MRI scan to assure that the heart 20 is stimulated by signals provided by the sensing/therapy module 44. The MRI detect module 48 detects the presence of MRI fields. Then, in step 60, the controller 42 changes the stimulation energy provided by the sensing/therapy module 44 from a first, pre-MRI energy state to a second, MRI mode energy state to assure capture of the tissue of the heart 20. In some embodiments, the controller 42 may be programmed to control the sensing/therapy module 44 to provide pacing pulses having a predetermined signal amplitude and/or duration in the presence of an MRI field. In some embodiments, the second energy state has a greater amplitude and/or duration than the first energy state, since the MRI fields can increase the capture threshold of the heart 20. The second energy state may be programmed into the controller 42, or the second energy state may be determined by the sensing/therapy module 44 using capture detection algorithm discussed above. Alternatively, the second energy state may be provided to the IMD 12 via the external device 19.

When the MRI detect module 48 senses the absence of the MRI fields (i.e., when the MRI scan is completed), the MRI detect module 48 sends a signal to the controller 42 to suspend the MRI mode of operation. Alternatively, the controller 42 may suspend the MRI mode of operation after a predetermined period of time (e.g., one hour) based on an anticipated length of the MRI scan. In any case, in step 62, the controller 42 maintains the stimulation energy provided by the sensing/therapy module 44 at the second energy state after the MRI scan. This is because the capture threshold of the heart 20 may remain elevated after the MRI scan, since the tissue of the heart 20 does not immediately recover from the effects of the MRI fields. This assures that proper pacing is maintained while the tissue is residually affected by the MRI scan.

In step 64, the controller 54 then commands the sensing/therapy module 44 to measure the capture threshold of the tissue of the heart 20. As discussed above, the sensing/therapy module 44 may deliver a sequence of pacing pulses of varying magnitude and/or duration to the tissue and sense the response of the tissue to the pacing pulses. The sensing/therapy module 44 may conduct the capture threshold test automatically after a programmed period of time from when the MRI detect module 48 senses that the MRI field is no longer present, or after a programmed period of time independent of when the MRI field was last detected. Alternatively, the sensing/therapy module 44 may conduct the capture threshold test in response to signals from the external device 19. The medical personnel controlling the external device 19 may manually determine the proper capture threshold based on signals generated by the sensing/therapy module 44 during the capture threshold test. If the determination of the capture threshold is not successful, then the sensing/therapy module 44 maintains the stimulation energy at the second energy state.

If the sensing/therapy module 44 determines the capture threshold successfully, then, in step 66, the controller 42 controls the sensing/therapy module 44 to adjust the stimulation energy provided to pace the heart 20 based on the measured capture threshold. This may be performed automatically by the IMD 12 or in response to signals provided by the external device 19. Thus, if the sensing/therapy module 44 determines that the capture threshold has decreased from the second energy state (i.e., the MRI mode stimulation state), the controller 42 reduces the energy state (i.e., the amplitude and/or duration) of the stimulation pulses to correspond to the decreased capture threshold. This assures that the draw on the energy storage device 40 is minimized while at the same time assuring proper energy and pace amplitude is provided to the heart 20 for stimulation.

In some embodiments, steps 54 and 56 are repeated by the IMD 12 until a physiological event occurs. For example, steps 54 and 56 may be periodically or intermittently repeated until the capture threshold returns to the first, pre-MRI stimulation energy state. This assures that the IMD 12 provides proper pacing stimulation until the heart 20 is no longer affected by the MRI fields. As another example, steps 54 and 56 may be repeated until the capture threshold remains steady for a programmed number of capture threshold tests. Thus, even if the capture threshold does not return to the first, pre-MRI stimulation energy state, the IMD 12 operates to provide pacing pulses at a level sufficient to stimulate the tissue.

In summary, the present invention relates to controlling energy delivered from an implantable medical device to stimulate tissue. Energy delivered to stimulate the tissue is changed from a first energy state to a second energy state during a magnetic resonance imaging (MRI) scan. The energy delivered is maintained at the second energy state after the MRI scan. A capture threshold of the tissue is then measured, and the level of energy delivered to the tissue is adjusted based on the measured capture threshold of the tissue. By monitoring the capture threshold after the MRI scan, the implantable medical device delivers a sufficient level of energy to stimulate the tissue when the tissue is residually affected by the MRI scan.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. For example, while the present invention has been described with regard to cardiac pacing, the principles of the present invention are also applicable to other types of systems with stimulation properties that may be altered by MRI fields, such as neurological therapy systems. In addition, while the system described uses electrical signals to stimulate tissue, other types of control agents may be employed to compensate for the effects of the MRI fields on the tissue, such as by chemical stimulation. Accordingly, the scope of the present invention is intended to embrace all such alternatives, modifications, and variations as fall within the scope of the claims, together with all equivalents thereof.

We claim:
1. An implantable medical device for delivering electrical stimulation to body tissue via a lead having at least one electrode, the implantable medical device comprising:
    sensing circuitry configured to receive cardiac or neural signals through the lead based on electrical activity of the tissue;
    therapy circuitry configured to deliver cardiac or neural electrical stimulation to the tissue through the lead, wherein the sensing and therapy circuitry is further configured to measure a capture threshold of the tissue;
    magnetic field detection circuitry configured to detect magnetic resonance imaging (MRI) scan fields; and
    control circuitry configured to change the energy delivered by the therapy circuitry from a normal energy state to an MRI mode energy state sufficient to capture the tissue including an adjustment of stimulus magnitude or duration of the cardiac or neural electrical stimulation when the magnetic detection circuitry detects a MRI scan field, and, after the magnetic field detection circuitry no longer detects the MRI scan field, to control the sensing and therapy circuitry to measure the capture threshold and then change the energy delivered by the therapy circuitry based on the capture threshold that was measured after the MRI scan field is no longer detected.

2. The implantable medical device of claim 1, wherein the control circuitry is configured to maintain the energy delivered by the therapy circuitry at the MRI mode energy level for a period of time after the magnetic field detection circuitry no longer detects the MRI scan field.

3. The implantable medical device of claim 1, wherein the control circuitry is configured to repeatedly adjust the energy delivered based on the measured capture threshold until the energy delivered returns to the normal energy state.

4. The implantable medical device of claim 1, wherein, to measure the capture threshold, the therapy circuitry is configured to deliver a sequence of pacing pulses of varying magnitude and/or duration to the tissue, and the sensing circuitry is configured to sense a response of the tissue to the pacing pulses.

5. The implantable medical device of claim 1, wherein the sensing circuitry is configured to measure the capture threshold of the tissue and the control circuitry is configured to adjust the energy delivered in response to a control signal from an external device.

6. The implantable medical device of claim 1, wherein the sensing circuitry, therapy circuitry, magnetic field detection circuitry, and control circuitry are included in a pulse generator.

7. The implantable medical device of claim 1, further comprising communication circuitry configured to communicate information about the measured capture threshold.

8. The implantable medical device of claim 1, wherein the MRI mode energy state has one or both of a signal magnitude and a duration that are respectively greater than the signal magnitude and the duration of the normal energy state.

9. The implantable medical device of claim 1, wherein the control circuitry is configured to change the energy delivered by the therapy circuitry from a first energy state to a second energy state sufficient to capture the tissue including an adjustment of stimulus magnitude or duration when the magnetic detection circuitry detects a MRI scan field, and, after the magnetic field detection circuitry no longer detects the MRI scan field, to control the sensing and therapy circuitry to measure the capture threshold and then change the energy delivered by the therapy circuitry from the MRI mode energy state to a post-MRI energy state based on the capture threshold that was measured after the MRI scan field is no longer detected.

10. The implantable medical device of claim 1, wherein:
the sensing circuitry is configured to receive cardiac signals through the lead based on electrical activity of the tissue; and
the therapy circuitry is configured to deliver cardiac electrical stimulation to the tissue through the lead, wherein the sensing and therapy circuitry is further configured to measure a capture threshold of the tissue during cardiac electrical stimulation.

11. The implantable medical device of claim 1, wherein:
the sensing circuitry is configured to receive neural signals through the lead based on electrical activity of the tissue; and
the therapy circuitry is configured to deliver neural electrical stimulation to the tissue through the lead, wherein the sensing and therapy circuitry is further configured to measure a capture threshold of the tissue during neural electrical stimulation.

12. An implantable medical device for delivering electrical stimulation to body tissue via a lead having at least one electrode, the implantable medical device comprising:
sensing circuitry operable to receive cardiac or neural signals through the lead based on electrical activity of the tissue;
therapy circuitry operable to deliver cardiac or neural electrical stimulation to the tissue through the lead, wherein the sensing and therapy circuitry is further operable to measure a capture threshold of the tissue;
magnetic field detection circuitry operable to detect magnetic resonance imaging (MRI) scan fields; and
control circuitry operable to set energy delivered by the therapy circuitry to stimulate the tissue from a normal energy state to an MRI mode energy state sufficient to capture the tissue including an adjustment of stimulus magnitude or duration of the cardiac or neural electrical stimulation when the magnetic detection circuitry detects the MRI scan fields, and, after the magnetic field detection circuitry no longer detects the MRI scan fields, to adjust the energy delivered based on the measured capture threshold of the tissue.

13. The implantable medical device of claim 12, wherein the control circuitry maintains the energy delivered by the therapy circuitry at the MRI mode energy level for a period of time after the magnetic field detection circuitry no longer detects the MRI scan fields.

14. The implantable medical device of claim 12, wherein the control circuitry repeatedly adjusts the energy delivered based on the measured capture threshold until the energy delivered returns to the normal energy state.

15. The implantable medical device of claim 12, wherein, to measure the capture threshold, the therapy circuitry delivers a sequence of pacing pulses of varying magnitude and/or duration to the tissue, and the sensing circuitry senses a response of the tissue to the pacing pulses.

16. The implantable medical device of claim 12, wherein the sensing circuitry measures the capture threshold of the tissue and the control circuitry adjusts the energy delivered in response to a control signal from an external device.

17. The implantable medical device of claim 12, wherein the sensing circuitry, therapy circuitry, magnetic field detection circuitry, and control circuitry are included in a pulse generator.

18. The implantable medical device of claim 12, and further comprising:
communication circuitry operable to communicate information about the measured capture threshold.

19. The implantable medical device of claim 12, wherein the MRI mode energy state has one or both of a signal magnitude and a duration that are respectively greater than the signal magnitude and the duration of the normal energy state.

20. An implantable medical device for delivering electrical stimulation to body tissue via a lead having at least one electrode, the implantable medical device comprising a control circuitry configured to:
in response to a presence of an MRI scan field, control the implantable medical device to deliver cardiac or neural electrical stimulation with an MRI mode energy state sufficient to capture the tissue; and
in response to an absence of the MRI scan field, change the MRI mode energy state to a post-MRI mode energy state based on a capture threshold when the MRI scan field is absent, and control the implantable medical device to deliver cardiac or neural electrical stimulation with the post-MRI mode energy state;
wherein the change from the MRI mode energy state to the post-MRI mode energy state includes an adjustment of stimulus magnitude or duration of the of the cardiac or neural electrical stimulation.

* * * * *